United States Patent [19]
Yuan et al.

[11] Patent Number: 6,147,135
[45] Date of Patent: Nov. 14, 2000

[54] FABRICATION OF BIOCOMPATIBLE POLYMERIC COMPOSITES

[75] Inventors: J. Jenny Yuan, Bridgewater; Arindam Datta, Hillsborough; Dennis D. Jamiolkowski, Long Valley, all of N.J.

[73] Assignee: Ethicon, Inc., Somerville, N.J.

[21] Appl. No.: 09/223,947

[22] Filed: Dec. 31, 1998

[51] Int. Cl.$^7$ .............. A61K 9/22; A61M 1/06; A61M 11/00
[52] U.S. Cl. ............ 523/105; 525/937; 604/891.1; 604/93; 604/175
[58] Field of Search ............ 528/328; 525/240, 525/937; 523/105; 604/891.1, 93, 175

[56] References Cited

U.S. PATENT DOCUMENTS

| | | | |
|---|---|---|---|
| 4,604,097 | 8/1986 | Graves, Jr. et al. | 623/11 |
| 5,092,884 | 3/1992 | Devereux et al. | 623/11 |
| 5,338,772 | 8/1994 | Bauer et al. | 523/115 |
| 5,397,816 | 3/1995 | Reilly et al. | 523/113 |
| 5,458,653 | 10/1995 | Davidson | 623/23 |
| 5,468,544 | 11/1995 | Marcolongo et al. | 428/224 |
| 5,490,962 | 2/1996 | Cima et al. | 264/22 |
| 5,578,046 | 11/1996 | Liu et al. | 606/151 |
| 5,626,611 | 5/1997 | Liu et al. | 606/230 |
| 5,674,286 | 10/1997 | D'Alessio et al. | 623/11 |
| 5,697,976 | 12/1997 | Chesterfield et al. | 623/11 |
| 5,721,049 | 2/1998 | Marcolongo et al. | 428/370 |
| 5,728,753 | 3/1998 | Bonfield et al. | 523/114 |

OTHER PUBLICATIONS

"Dynamic Mechanical Analysis To Evaluate Annealing Conditions For Polypropylene Filaments" Authors—Arindam Datta, Jianguo J. Zhou, Jenny Yuan, Andrea Monisera. Apr., 1997; SPE ANTEC Toronto, California.

*Primary Examiner*—Nathan M. Nutter

[57] ABSTRACT

Composite materials formed from biocompatible polymer fibers and biodegradable polymers are disclosed. The heat treatment conditions for the reinforcing fibers are described so that the mechanical properties of the fibers can be retained during composite consolidation process. The processing conditions and set-ups to consolidations are constrained to the temperatures lower than fiber heat treatment temperatures. The reinforcing fibers are restrained under tension so that the minimum relaxation occurs during consolidation process.

6 Claims, 2 Drawing Sheets

FABRICATION OF BIOCOMPATIBLE POLYMERIC COMPOSITES

FIELD OF THE INVENTION

The field of art to which this invention relates is biocompatible polymers, more specifically, biocompatible polymer fiber-reinforced, polymeric composites for use in medical devices; and a method for making them.

BACKGROUND OF THE INVENTION

Fracture fixation is a common surgical operation to address bone fractures by attaching a reinforcing rod or a plate or a cage to a fractured bone so that the broken ends may be stabilized to promote fusion and consequent healing.

Metal implants have often been used because of their high stiffness and strength that stabilizes the fracture site during tissue healing. However, several issues still remain. Metal implants, being much stiffer than bone, become the primary load-bearing member thereby protecting the bone from stress, thus resulting in stress shielding. It has been observed that moderate stress is beneficial to bone tissue growth. If the metal implant is not removed, the extended stress shielding will eventually weaken the bone, resulting in bone atrophy through decalcification or osteoporosis. Therefore, it is often necessary to perform a second surgical procedure to remove metal implants after the bone tissues have healed. This second surgical procedure can result in pain and discomfort.

The use of bioabsorbable materials for fracture fixation has the potential to eliminate the necessity of a second operation and help alleviate the negative effect of stress shielding. Specifically designed bioabsorbable materials can have mechanical properties that begin to approach those of bone in some applications (but certainly not all) and are strong enough to stabilize the fracture. As time progresses, the bioabsorbable material implant gradually decreases its stiffness and strength due to biodegradation. At the same period of time, the bone fracture heals. During the course of these two overlapping events, the mechanical stresses from daily activity and exercise are gradually transferred from the degradable bioabsorbable implant to the healing bone tissue.

Bioabsorbable polymeric materials have also been used in the form of pins, rods, anchors and staples for a variety of medical applications including orthopaedic devices. They are usually made by injection molding or extrusion. However, relatively low stiffness and strength of bioabsorbable devices compared with metallic implants have limited their use to low-load bearing applications or non-load bearing applications.

Considerable effort has been applied towards increasing the stiffness and strength of bioabsorbable materials. Several methods have been reported using various composite technologies in attempt to increase the strength and stiffness of bioabsorbable polymers by using different methods and types of reinforcements.

One method using composite technology has been to incorporate a strong and stiff non-absorbable inorganic structural fiber or partiles, made from carbon or glass, as reinforcing agents in a bioabsorbable polymeric matrix. The disadvantage of this system is that the non-absorbable fibers stay behind in the body tissue after the bioabsorbable polymer has been absorbed by the body and in the long run, may cause tissue reaction or other undesirable effects, such as unwanted migration.

Another composite preparation method has been to incorporate inorganic bioabsorbable glass or ceramic reinforcement such as fibers or particles. The lack of fiber-matrix interfacial bonding remains a major issue, and may cause poor load transfer mechanism between the fiber and the incompatible matrix. Poor interface problems are accentuated when implants are placed in human body and may cause the implant to fail prematurely.

Another composite preparation method has been to reinforce bioabsorbable polymers with different polymer fibers. The reinforcing polymer fibers, are usually stiffer and stronger (usually having higher glass transition and melting temperatures) than the matrix. In yet another method, highly drawn fibers of polylactide (PLA) or polyglycolide (PGA) were fused to develop bioabsorbable polymeric device with increased stiffness and strength.

Several patents describe bioabsorbable composites and the way of making them. U.S. Pat. No. 5,674,286 describes bioabsorbable composites for use in medical implants. The composite materials are composed of a hybrid yarn of intimately co-mingled reinforcing fibers of a crystalline polymer and matrix fibers of a polymer having a glass transition temperature lower than the melting point of the fiber crystalline polymer. The hybrid yarn is heated under pressure to a processing temperature between the glass transition temperature of the matrix fibers and the melting temperature of the crystalline polymer to form the continuous fiber reinforced composites.

U.S. Pat. No. 5,092,884 describes a composite structure having two or more biocompatible fiber polymers, in which at least, one of the reinforcing fibers is nonabsorbable. The fiber is woven into a mesh and then encapsulated with at least one biodegradable polymer.

U.S. Pat. No. 4,279,249 describes an osteosynthesis part made from a bioabsorbable composite made from a matrix of lactic acid homopolymer or a copolymer high in lactic acid unit with embedded discrete reinforcing elements made from glycolic acid or copolymers predominant in glycolic acid unit.

U.S. Pat. Nos. 5,578,046 and 5,626,611 describe bioabsorbable composite materials having a core portion formed from a first bioabsorbable material and the shell portion of the second bioabsorbable material joined to the core portion. The first bioabsorbable polymer has a higher rate of bioabsorption than the second bioabsorbable polymer. The composite filaments can also be made into woven and non-woven sheets.

U.S. Pat. Nos. 5,468,544 and 5,721,049 describes layered composite materials formed from bone bioactive glass or ceramic fibers and structural fibers and bioabsorbable polymers.

U.S. Pat. No. 5,728,753 describes composites suitable for use as prostheses for attachment to soft tissue, such as cartilage, tendons, skin, tympani membrane and gingiva, as well as cancellous or trabecular bone, based on combinations of polyolefinic binders with certain bioactive glass particles and fibers.

U.S. Pat. No. 5,338,772 describes an implant material, which is based on porous composite materials formed by calcium phosphate ceramic particles bridged by bioabsorbable polymers.

U.S. Pat. No. 4,604,097 describes spun or drawn glass fibers for use in the areas of medical devices as reinforcement for bioabsorbable polymeric orthopedic and dental implants.

In the formation of reinforced biocompatible organic composites, the matrix polymer is melted, forced generally under pressure to flow around the reinforcing fibers and cooled. The consolidation temperature of the matrix can be either below or above the Tg of the fiber material. Unfortunately, the melting temperature of the matrix may cause the biocompatible organic fibers to partially relax their molecular orientation, thereby losing their strength and stiffness, which consequently affect the properties of the composite.

Thus it is an object of the present invention to provide biocompatible organic polymeric composites with one or more improved properties and a method for producing these composites.

SUMMARY OF INVENTION

We have discovered a process for forming a polymer based biocompatible composite that will be consolidated at an elevated temperature comprising the steps of (a) restraining and heating biocompatible organic polymeric fibers to a temperature that is above the elevated temperature of consolidation but below the melting temperature of the biocompatible organic fibers for a time sufficient to stabilize the biocompatible organic fibers; (b) contacting the heat treated fibers with a polymeric matrix to provided a preform; and (c) consolidating the preform by heating the preform to the consolidation temperature for a time sufficient to consolidate the preform and provide a composite. The composites formed by this process will have superior mechanical properties by retaining higher values of tensile modulus and tensile strength of the reinforcing fibers as compared to composites in which the fiber were not heat treated.

In a further embodiment of the present invention, we have discovered a process for forming a polymer based biocompatible composite that will be consolidated at an elevated temperature comprising the steps of (a) contacting biocompatible organic polymeric fibers with a polymeric matrix to provide a preform; (b) restraining the biocompatible organic polymeric fibers in the preform and consolidating the preform by heating the preform to the consolidation temperature below the melting temperature of the biocompatible organic fibers for a time sufficient to consolidate the preform and provide a composite. The composites formed by this process will have superior mechanical properties by retaining higher values of tensile modulus and tensile strength of the reinforcing fibers as compared to composites in which the fibers were not restrained while the prepreg was consolidated.

Another embodiment of the present invention provides methods of making fiber-matrix prepregs or green forms which includes: melt impregnation, powder coating, solution coating and commingling with matrix fibers; filament windings, weaving, and braiding to provide composite preforms followed by composite consolidation.

DETAILED DESCRIPTION

What follows is a description of the composite pre-consolidation and consolidation techniques which will provide organic biocompatible composites that have superior mechanical properties by retaining higher values of tensile modulus and tensile strength of the reinforcing fibers. One process involves heat treating organic biocompatible fibers at temperatures higher than the consolidation temperature of the composite matrix to stabilize fiber's structures prior to consolidating the polymer-polymer composite. Alternatively, composite can be improved by restraining the reinforcing organic biocompatible fibers during the consolidation of the composite.

The composite of the present invention is a biocompatible organic polymer matrix reinforced with a biocompatible organic fiber to form a composite. The composite of the present invention is generally formed by use of compression molding in a press under a dry inert environment (under nitrogen, argon, etc.) or under vacuum, at high enough temperatures and long enough residence times to consolidate the composite from the fiber-matrix preform. Alternately, the composite of the present invention is formed by use of an autoclave, under a dry inert environment or under vacuum, at high enough temperatures and long enough residence times to consolidate the composite from the fiber-matrix preform. The reinforcing fibers are generally semi-crystalline bioabsorbable polymers while the matrix materials are generally either amorphous or semi-crystalline bioabsorbable polymers. In conventional composites, such as glass or carbon reinforced composites, the reinforcing fibers are not affected by consolidation temperature of the matrix. However, the fibers in composites in which both the matrix and the fibers are biocompatible or bioabsorbable polymers, the consolidation temperatures of the matrix can be between glass transition (Tg) and melting temperature (Tm) of the reinforcing fibers. At the consolidation temperatures of the matrix, the semi-crystalline fibers begin to lose some of their orientation as they are heated between their Tg's and Tm's. For the purpose of the present invention, we are describing a pre-consolidation heat treatment for the fiber and/or a consolidation process wherein the fibers are restrained during the consolidation process. Both of these processes will reduce or minimize relaxation of fiber orientation and allow for retaining the superior tensile properties of the fiber. Additionally restraining the fibers will control or avoid shrinkage of the fibers during heat treatment and/or consolidation.

Figure 1:
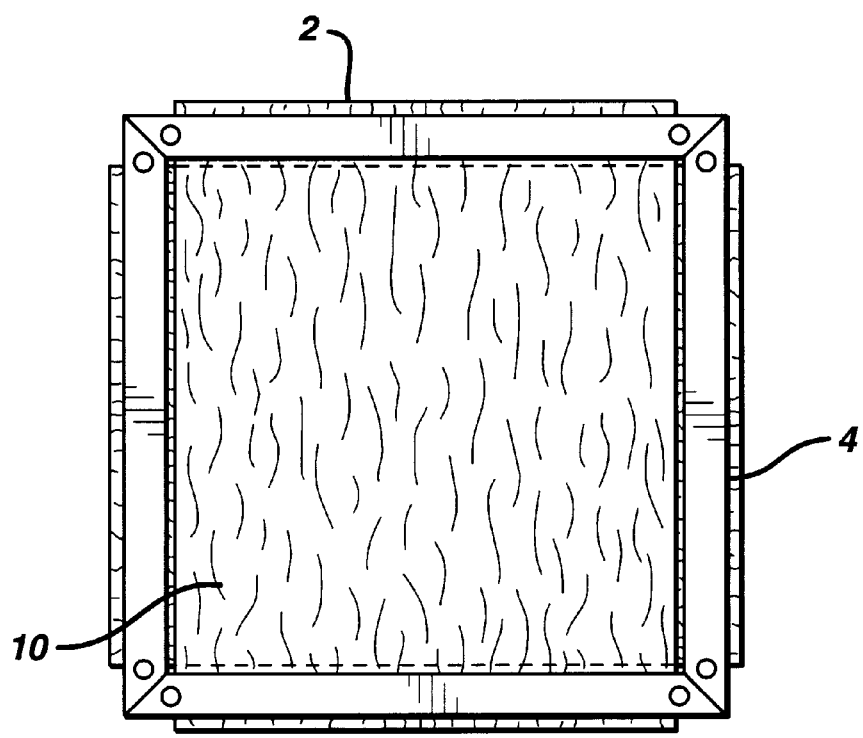
FIG. 1 illustrates a top view of the fibers end 2 of the prepreg 10 being restrained by the restraining bars 4 during the formation of a composite.
Figure 2:
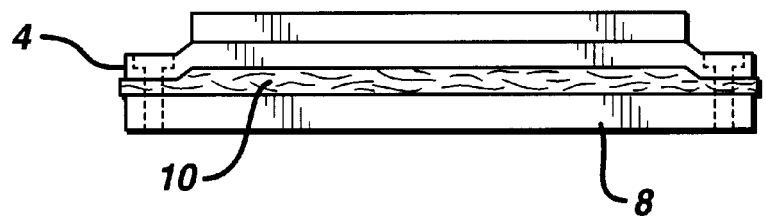
FIG. 2 illustrates a side view of the prepreg 10 with the restraining bars 4 attached to frame 8.
Figure 3:
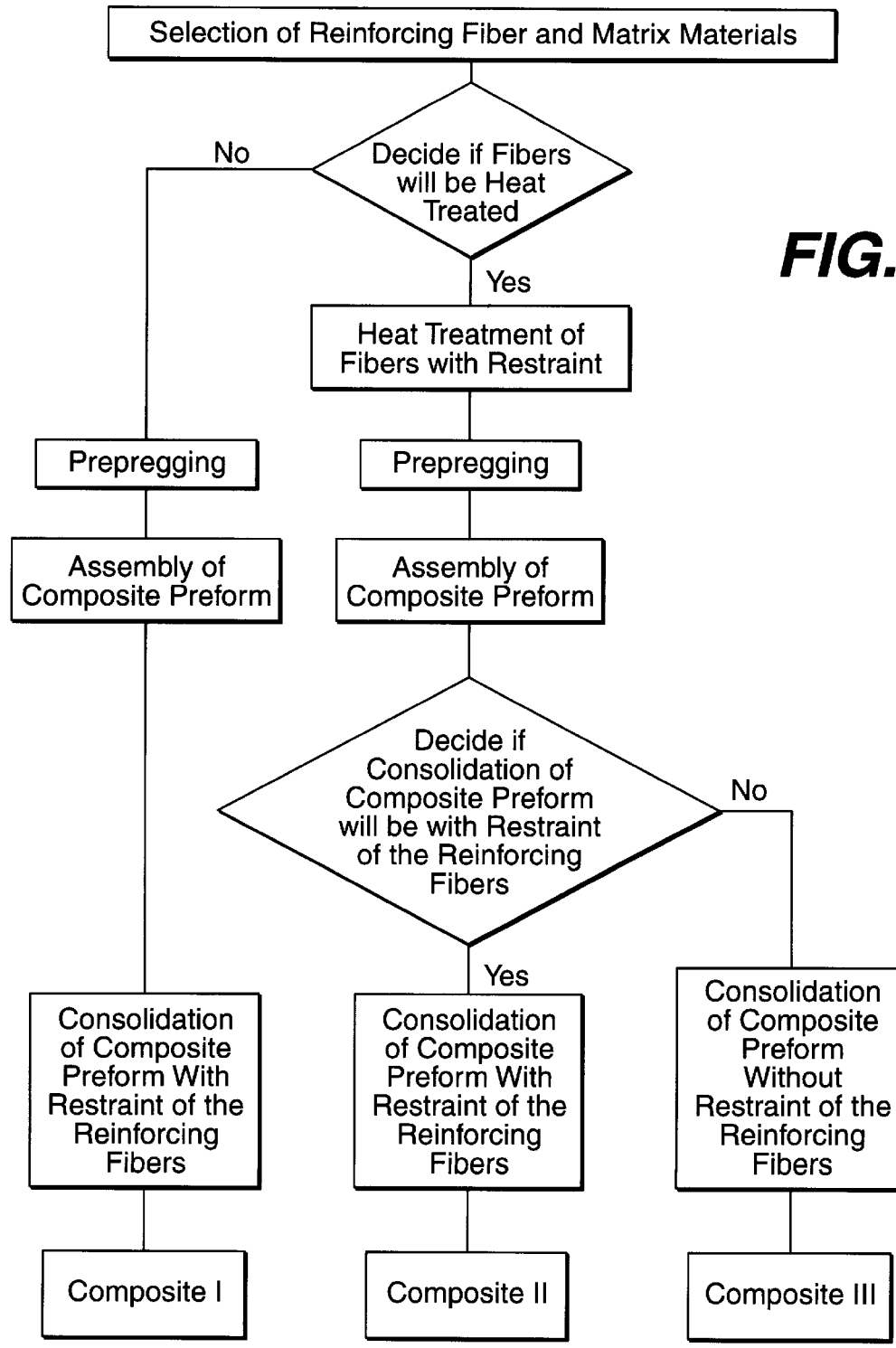
FIG. 3 provides a flow chart generally describing the three processes described in the present invention.

The fibers can be restrained during the heat treatment or the consolidation by a variety of means including but not limited to mechanical clamps or rack systems (such as the annealing racks used in suture processing). One suitable system for restraining the fibers in a prepreg or preform is illustrated in FIGS. 1 and 2. Not all of the fiber that are used in the preform need to be restrained, especially if the final composite is designed to have different properties along different axis or planes, or if a plurality of different fiber types will be employed in the composite. The restraint of the fiber may involve (1) controlling the amount of shrinkage (i.e. allowing only a limited shrinkage to allow a better match of composite and/or fiber properties); (2) maintaining the fiber with no initial tension (as the fiber is heat treated, however, tension will develop); (3) restraining the fiber under tension (to retain the fibers initial properties to a greater extent); or (4) possibly redrawing the fibers (generally less than 10 percent if the fiber has been drawn to at least its natural draw) during the restraint. The optimum conditions for a biocompatible fiber will depend on the temperature that the fiber will be exposed to during consolidation and the fiber's chemistry and morphology. Those skilled in the art will readily appreciate that by using conventional experimental techniques such as dynamic scanning calorimetry or differential thermal analysis, one can determine the Tg of the fiber in question. The fibers response to the thermal cycle in either process can be determined by a variety of approaches such as the experimental procedure described in Example 1 or by dynamic mechanical analysis as is described in Example 4.

In the first embodiment of the present invention the heat treatment is carried out at least about 5° C. above the matrix consolidation temperature and at least about 10° C. below the Tm of the fiber. Preferably the heat treatment will be carried out at least about 10° C. above the matrix consolidation temperature and at least about 20° C. below the Tm of the fiber. More preferably heat treatment will be carried out at least about 10° C. above the matrix consolidation temperature and at least about 30° C. below the Tm of the fiber. The time of pre-consolidation heat treatment will be less than about 10 hours, preferably less than about 6 hours and more preferably in the range of from about 4 hours to about 2 minutes. Those skilled in the art will appreciate that optimum times and temperatures may be readily determined by routine experimentation.

The polymeric biocompatible fibers (pre-consolidation heat-treated fibers and non-heat-treated fibers) are impregnated with matrix materials through powder, melt or solution processes to form prepregs. Before or after impregnation of the fibers with the matrix material or fibers commingled with matrix fibers (fibers that melt to form the matrix), the fibers may be formed into a textile such as a woven, knitted or braided textile prior to consolidation of the composite. The fiber-matrix prepregs are laminated in multiple stacks according to a pre-determined composite design including fiber orientation and thickness. In one embodiment of the present invention the edge of the preform is restrained, thereby restraining the fibers during consolidation as previously described. The preform is then consolidated by using a compression molder or autoclave and goes through the consolidation cycle. Depending on the specific material system, a consolidation cycle often involves following steps (1) introducing vacuum; (2) heating to pre-set consolidation temperature(s); (3) applying pressure during heating; (4) consolidating the preform at pre-set temperature(s) under high pressure; and (5) cooling under pressure. The optimum consolidation condition is to form a composite with no voids, with uniform fiber distribution, and with superior composite properties.

For the purpose of this invention, it is preferred that prior to composite consolidation, preforms are restrained and this together with appropriate consolidation conditions results in controlled fiber shrinkage or relaxation of orientation. Generally fiber shrinkage will be minimized to obtain optimum composite properties. For example fiber-matrix prepregs may be laminated in multiple stacks according to a pre-determined composite design. The fibers in every lamina may be restrained by clamping in a mold as shown in FIG. 2. However, the fibers could be selectively restrained to provide specific properties to the final composite along a specific axis or the like. Preferably, the fibers will be restrained under a specific tension during consolidation. The preform is then consolidated by using compression molder or autoclave and goes through the consolidation cycle.

The reinforcing fibers and the matrix are formed from a set that meets certain requirements. The fibers are formed with polymers and copolymers that have Tms, that are higher than the polymers and copolymers used to form the matrix. Of course, amorphous matrix materials will not have a crystalline melting transition, therefore, is required that the Tm of the fiber is higher than the Tg of the amorphous matrix material and that the Tm of the fiber is higher than the temperature at which the amorphous matrix material becomes soft or viscous enough to be consolidated with the fibers. For some applications it may be preferred for the matrix material to be rendered into a viscous liquid to provide suitable consolidation. Suitable organic biocompatible polymer that can be used to make the fibers and matrix are well known in the art. These biocompatible polymers include both bioabsorbable and biostable polymers.

Examples of suitable organic biocompatible bioabsorbable polymers that could be used include polymers selected from the group consisting of aliphatic polyesters, poly (amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, and blends thereof. For the purpose of this invention aliphatic polyesters include but are not limited to homopolymers and copolymers of lactide (which includes D- and L- lactic acids; D-, L-, and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, α,α-diethylpropiolactone, ethylene carbonate, ethylene oxalate, 3-methyl-1,4-dioxan-2,5-dione, 3,3-diethyle-1,4-dioxan-2,5-dione, 6,8-dioxabicycloctane-7-one, 2,5-diketomorpholine, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof. Poly(iminocarbonate) for the purpose of this invention include as described by Kemnitzer and Kohn, in the *Handbook of Biodegradable Polymers,* edited by Domb, Kost and Wisemen, Hardwood Academic Press, 1997, pages 251–272. Copoly(ether-esters) for the purpose of this invention include those copolyester-ethers described in "Journal of Biomaterials Research", Vol. 22, pages 993–1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4;208,511; 4,141,087; 4,130,639; 4,140,678; 4,105, 034; and 4,205,399 (incorporated by reference herein). Polyphosphazenes copolymers (such as co-, ter- and higher order mixed monomer based polymers) made with L-lactide, D-lactide, meso-lactide, L-lactic acid, D-lactic acid, glycolide, glycolic acid, para-dioxanone, trimethylene carbonate and ε-caprolactone such as are described by Allcock in *The Encyclopedia of Polymer Science,* Vol. 13, pages 31–41, Wiley Intersciences, John Wiley & Sons, 1988 and by Vandorpe, Schacht, Dejardin and Lemmouchi in the *Handbook of Biodegradable Polymers,* edited by Domb, Kost and Wisemen, Hardwood Academic Press, 1997, pages 161–182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons. Polyoxaesters polyoxaamides and polyoxaesters containing amines and/or amido groups are described in one or more of the following U.S. Pat. Nos. 5,464,929; 5,595,751; 5,597, 579; 5,607,687; 5,618,552; 5,620,698; 5,645,850; 5,648, 088; 5,698,213; and 5,700,583; (which are incorporated herein by reference). Polyorthoesters such as those described by Heller in *Handbook of Biodegradable Polymers,* edited by Domb, Kost and Wisemen, Hardwood Academic Press, 1997, pages 99–118 (hereby incorporated herein by reference).

Examples of suitable organic biocompatible biostable polymers with relatively low chronic tissue response include but are not limited to polymers selected from the group consisting of polyurethanes, polyolefins, polyesters, poly(meth)acrylates, polyvinyl fluorides, nylons and combinations thereof. Suitable polymers include but are not limited to polymers selected from the group consisting of polyolefins (such as polyethylene and polypropylene including atactic, isotactic, syndiotactic, and blends thereof as well as, polyisobutylene and ethylene-alphaolefin copolymers); polyesters (such as polyethylene terephthalate and polybutylene terephthalate); acrylic polymers and copolymers, vinyl halide polymers and copolymers (such as polyvinyl chloride); polyvinyl ethers (such as polyvinyl methyl ether); polyvinylidene halides (such as polyvinylidene fluoride and polyvinylidene chloride); polyacrylonitrile; polyvinyl ketones; polyvinyl aromatics (such as polystyrene); polyvinyl esters (such as polyvinyl acetate); copolymers of vinyl monomers with each other and olefins, (such as etheylene-methyl methacrylate copolymers, acrylonitrile-styrene copolymers, ABS resins and ethylene-vinyl acetate copolymers); polyamides (such as nylon 4, nylon 6, nylon 66, nylon 610, nylon 11, nylon 12 and polycaprolactam); alkyd resins; polycarbonates; polyoxymethylenes; polyimides; polyethers; epoxy resins, polyurethanes; rayon; and rayon-triacetate. Polyamides for the purpose of this application would also include polyamides of the form —NH—$(CH_2)_n$—CO— and NH—$(CH_2)_x$—NH—CO—$(CH_2)_y$—CO, wherein n is preferably an integer in from 6 to 13; x is an integer in the range of form 6 to 12; and y is an integer in the range of from 4 to 16. The list provided above is illustrative but not limiting.

The fibers used in the present invention may be made using a variety of processes that provide fibers with the desired properties (such as modulus, tensile strength, elongation etc.). Those skilled in the art of fiber processing are well versed in the art of extrusion, solution spinning etc. which may be used to provide polymer based fibers. These fibers may be oriented or drawn using conventional process to provide the desired degree of modulus, strength, elongation, etc. Generally, a fiber orientation process is used to improve the properties of the reinforcing fibers. The fibers can be oriented using a variety of drawing technologies such as single, multiple or continuous drawing steps with or without heating zones and/or relaxation. Fibers are typically drawn in the range of from about 1.5 to about 20 times their original length in the drawing process and more typically from about 2 to about 7 times the fibers original length. Additionally, these fibers may be post treated with various annealing, scouring, coating or surface treatment steps. For example from poly(p-dioxanone) fibers are most preferably oriented in the range of about 4 to about 7 times as is described in Doddi et al. in U.S. Pat. No. 4,052,988(hereby incorporated by reference herein). The temperature of orientation for poly(p-dioxanone) is between 25 and 90° C. with preferred range being 40 and 80° C. For semicrystalline fibers of a copolymer of 95 mole percent lactide and 5 mole percent glycolide the fibers are drawn in the range of about 4 to about 7 times and orientation is preferably performed at a temperature in the range of from about 100 to about 160° C. and most preferably in the range of from about 120° C. to about 150° C.

For example, fiber can be made from a polymer or copolymer containing from about 50 to about 100 mole percent glycolide and preferably will contain at least 80 mole percent glycolide. If the copolymers have a non-random sequence distribution (i.e. block copolymers or the like) the compositional ranges could be expanded. Of particular utility for use as absorbable matrix materials are aliphatic amorphous polyesters such as racemic D,L-lactide copolymers, as well as, random mid-range poly(lactide-co-glycolide) copolymers. For example the amorphous random copolymers of lactide (or lactic acid) and glycolide (or glycolic acid), can be formed from with each component varying from about 30 and about 75 mole percent. The matrix polymers may also be semicrystalline polymers, copolymers and/or blends thereof based on lactide, $\epsilon$-caprolactone, p-dioxanone and/or trimethylene carbonate. Preferred low melting semicrystalline matrix material are copolymers containing at least about 50 and more preferably at least 70 mole percent of repeat units based on poly($\epsilon$-caprolactone), and/or poly(p-dioxanone) copolymerized with lactide, trimethylene carbonate, glycolide and combinations thereof. Preferred high melting point semicrystalline matrix materials are copolymer containing in the range from about 80 to about 90 mole percent of glycolide and/or lactide copolymerized with poly($\epsilon$-caprolactone), poly(trimethylene carbonate), poly(p-dioxanone) and combinations thereof.

The fiber can be made from a polymer or copolymer containing greater than 75 to about 100 mole percent lactide and preferably at least 80 mole percent. If the copolymers have a non-random sequence distribution (i.e. block copolymers or the like) the compositional ranges could be expanded. Of particular utility for use as absorbable matrix materials are aliphatic amorphous polyesters such as racemic D,L-lactide copolymers, as well as, random mid-range poly(lactide-co-glycolide) copolymers. For example the amorphous random copolymers of lactide (or lactic acid) and glycolide (or glycolic acid), can be formed from with each component varying from about 30 and about 75 mole percent. The matrix polymers may also be semicrystalline polymers, copolymers and/or blends thereof based on lactide, glycolide, $\epsilon$-caprolactone, p-dioxanone and/or trimethylene carbonate. Preferred low melting semicrystalline matrix material are copolymers containing at least about 50 and more preferably at least 70 mole percent of repeat units based on poly($\epsilon$-caprolactone), and/or poly(p-dioxanone) copolymerized with lactide, trimethylene carbonate, glycolide and combinations thereof.

Additionally, if the fiber is made from a polymer or copolymer containing about 60 to about 100 mole percent poly(p-dioxanone) and preferably at least 80 mole percent, the matrix can be selected from polymer, copolymers and blends containing poly($\epsilon$-caprolactone), poly(p-dioxanone) and poly(trimethylene carbonate).

Here we present a few cases of possible combinations of composites made from bioabsorbable polymer matrix reinforced with bioabsorbable polymer fiber in order to demonstrate the relation between pre-consolidation heat treatment temperature for the fiber and consolidation temperature for the matrix. For example, a composite may be made from poly(p-dioxanone) fibers with matrix made from poly($\epsilon$-caprolactone) or copolymers containing at least 30 mole percent of $\epsilon$-caprolactone. Generally the melting point of a poly($\epsilon$-caprolactone) homopolymer or a copolymer containing at least 30 mole percent $\epsilon$-caprolactone will be 60° C. or lower. Composites containing these polymers as the matrix material will be consolidated at a temperature at least about 2° C. but preferably about 7° C. higher than the melting point of these polymers. The melting point of semicrystalline poly(p-dioxanone) reinforcing fibers will generally be about 120° C. Therefore, the poly(p-dioxanone) fibers may be heat treated at a temperature in the range of from about 65° C. to about 100° C. and preferably the fibers will be heat treated at a temperature in the range of from about 70° C. to about 95° C. Preferably the poly(p-dioxanone) fibers will be heat treated while being restrained to maximize the retention of tensile strength.

Another example of a composite that may be made following the process of the present invention is a composite made from semi-crystalline reinforcing fibers of a copolymer of 95 mole percent lactide and 5 mole percent glycolide and a matrix of poly(p-dioxanone). The melting point of poly(p-dioxanone) matrix is approximately 108° C. Thus the consolidation temperature of the composite will be at least about 110° C. and preferably at least 120° C. The melting point of semi-crystalline of 95 mole percent lactide and 5 mole percent glycolide is 165° C. In such a case the pre-consolidation heat treatment temperature of the fibers will be in the range of from about 125° C. to about 150° C. and preferably will be in the range of from about 130° C. to about 140° C.

In the case of those biocompatible composites consisting of biocompatible but not bioabsorbable fibers and bioabsorbable matrix, the fiber can be made from polyamide or polyethylene terepthalate and the matrix can be selected from polymer, copolymers and blends containing poly($\epsilon$-caprolactone), poly(p-dioxanone) and poly(trimethylene carbonate) or copolymers containing at least 40 or preferably 60 mole percent of poly($\epsilon$-caprolactone), poly(p-dioxanone) and poly(trimethylene carbonate) with poly (lactide) and poly(glycolide). Additionally, the matrix materials can also be composed of copolymers of poly (lactide) and poly(glycolide), in which the content of each component may vary between 10 and 90 mole percent. If the fibers are made from polypropylene or polyethylene, the matrix can be selected from polymer, copolymers and blends containing poly($\epsilon$-caprolactone), poly(p-dioxanone) and poly(trimethylene carbonate) or copolymers containing at least 40 or preferably 60 mole percent of poly ($\epsilon$-caprolactone). Examples of devices made from the novel absorbable composite, include but are not limited to, orthopedics devices (such as join replacement prosthesis, vertebral discs, pins, rods, nails, anchors, cages, screws, and plates for hard and soft tissue fixation); tissue engineering structures (such as tissue scaffolds for in vivo and in vitro tissue regrowth, augmentation and repair); and surgical devices (such as staples, arrows, pledgets, catheters, clamps, hooks, buttons, snaps, couplers, vascular and urological stents, valves, and clips).

In another embodiment of the present invention, the polymers and blends that are used to form the composite can be used as a drug delivery matrix. To form this matrix, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anti-inflammatory agents; hormones such as steroids; bone regenerating growth factors; and naturally derived or genetically engineered proteins, polysaccharides, glycoproteins, or lipoproteins.

Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

Additionally, radio-opaque markers may be added to the composite to allow imaging of the composite after implantation.

The following examples are illustrative of the principles and practice of this invention, although not limited thereto. Numerous additional embodiments within the scope and spirit of the invention will become apparent to those skilled in the art.

EXAMPLE 1

This example describes the effect of heat treatment on fibers made from 10/90 polylactide-co-glycolide (PLA/PGA) copolymer. The heat treatment temperature is chosen to be in the range where matrices such as poly($\epsilon$-caprolactone) (PCL) or poly(p-dioxanone)(PDS) would be consolidated if they are to form a composite with fibers made from 10/90 PLA/PGA copolymer.

The process of making multifilament fibers from a copolymer of 90 mole percent glycolide and 10 mole percent lactide is described next. The inherent viscosity of the polymer is 1.4 dL/g as determined in hexafluroisopropanol at 25° C. at a concentration of 0.1 g/dL. A one inch diameter vertical extruder with length to diameter ratio of 12 is fitted with a melt pump and a 14 hole die to obtain a 14 filament extrudate. The diameters of the die hole are 0.020 inches. The extrudate passes through a chimney before being drawn by godet rolls and are wound and collected on 6 inch diameter spools mounted on take up rolls. The multifilament fibers are processed using the conditions listed in Table 1.

TABLE 1

| Parameters | Value |
| --- | --- |
| Feed Zone | 216° C. |
| Transition Zone | 227° C. |
| Metering Zone | 227° C. |
| Pump | 232° C. |
| Adapter and clamp | 238° C. |
| Die | 243° C. |
| Chimney | 243° C. |
| Melt Pressure | <5000 psi. |
| Screw Speed | 15 rpm |
| Pump Speed | 10 rpm |
| Godet Speed | 1805 rpm |

The 14 filament extrudate or yarn is collected and stored under inert nitrogen atmosphere. The filaments will be further drawn by the following process. In the drawing process, the yarns are drawn at a speed ratio of 1.4 with the feed rolls being at 88° C. and the draw rolls being at 110° C.

The yarns pass through a third roll at room temperature with no change in drawing speed from the draw rolls. The resultant yarn has a denier of 2 gms/filament.

These (10/90 PLA/PGA copolymer) fibers may be used as the reinforcing elements in other absorbable polymers matrices such as PCL, PDS, etc. The consolidation temperatures will generally be higher than the glass transition temperature, Tg, of the fiber, which is around 40° C. and will cause molecular relaxation during consolidation process, resulting in modified mechanical properties. The effects of different heat treatment temperatures are presented here in Table 2. Also presented in Table 2 is the effect of relaxation. Relaxation of a pre-determined value is obtained by winding the 90/10 PLA/PGA filaments on a rack whose length can be adjusted by moving one of the end bars and then adjusting the movable bar by the pre-determined value to create a slack in the wound filament. Relaxation experiments can assists in understanding of what would happen to the properties of 10/90 PLA/PGA fibers if they were allowed to shrink during consolidation. The heat treatment conditions are: (1) 0 percent relaxation at a heat treatment temperature of 115° C. for 6 hours, and (2) 0 percent, 3 percent and 9 percent relaxation at heat treatment temperature of 130° C. for 6 hours.

Table 2 demonstrates moderate drop in modulus for heat treatment at both 115 and 130° C. with 0 percent relaxation and at 130° C. with only 3 percent relaxation. However, the drop in modulus is very high for 9 percent relaxation at 130° C. The yield strength shows significant drop with increase in temperature from 115° C. to 130° C. However, the effect of higher relaxation is more severe. The failure strength shows no significant change or an increase in its value at both 115 and 130° C. and for 3 percent relaxation at 130° C. Again at higher relaxation of 9 percent, there is a large or significant drop in failure strength. Unrestrained fibers would be expected to shrink significantly greater than 9 percent.

TABLE 2

Tensile Properties of untreated and heat treated Viaryl 28 denier Fibers

| Materials | Modulus (ksi) | Yield Strength (ksi) | Failure Strength (ksi) |
|---|---|---|---|
| Untreated | 2100 (100) | 49.2 (2.4) | 124.9 (5.7) |
| 115° C.-0% | 2010 (88) | 35.0 (2.9) | 137.1 (6.1) |
| 130° C.-0% | 2040 (110) | 32.8 (2.5) | 130.2 (7.8) |
| 130° C.-3% | 2030 (150) | 29.1 (1.4) | 143.9 (5.7) |
| 130° C.-9% | 1600 (110) | 22.1 (1.8) | 118.8 (7.5) |

The standard deviations are provided in parenthesis.

EXAMPLE 2

In another experiment, the 2 dpf 10/90 PLA/PGA fibers of Example 1 without any heat treatment were cut to 200 mm length. The fibers were placed between two plates and a pressure of 250 psi was applied for 10 minutes at 100° C. The fiber lengths were re-measured and it was found that on an average the fibers shrank by 10 percent from its original length. In the absence of the friction between the fibers and the plates, the fibers would be expected to shrink even more.

EXAMPLE 3

In Example 1 and 2, the effect of consolidating the 10/90 PLA/PGA fibers was shown to be shrinkage in the length of the fibers. It was also demonstrated that shrinkage in length of the fibers is associated with reduced mechanical properties especially if the reduction in length was large. In this example, the effect of consolidation conditions on fibers that have undergone heat treatment at temperatures above consolidation temperatures will be presented through the simulation of different processes using a dynamic mechanical analyzer.

A 10/90 PLA/PGA fiber having a circular cross-section area of 0.00051 square mm. and a length of 15 mm was held in the grip between a fixed clamp and a vibrating clamp in a dynamic mechanical analyzer. The vibrating clamp can oscillate at a frequency of 1 Hz at an oscillating amplitude of 5 micrometers. A base force of 5 grams was applied to the fiber so that it remained under tension (to avoid slack during testing). The fiber was heated at two separate heat treatment conditions of 140° C. for 8 hours and 130° C. for 8 hours. In both cases, the fibers were cooled to room temperature. The heat treated fibers were re-heated to 125° C. for 25 minutes to simulate consolidation parameters and then cooled to room temperature. The response of the 10/90 PLA/PGA fiber to the simulated thermal cycle representing consolidation is obtained as its modulus.

The results of fibers as a function of different thermal treatments are summarized in Table 3.

TABLE 3

| | Initial base line properties values at 30° C. | Property Values at 33° C. after 8 hrs heat treatment at 130° C. | Property Values of heat treated at 32° C. after undergoing consolidation conditions of 125° C. for 25 minutes |
|---|---|---|---|
| Modulus | 1.83 E 10 Pa | 1.83 E 10 Pa | 1.84 E 10 Pa |
| Shrinkage | | 7.9% from base line | 0.7% from heat treated fibers |

In this experiment, the fibers were partially constrained but still were able to shrink in length. Even then, it is clearly demonstrated that heat treatment at temperatures higher than consolidation temperature prior to consolidation results in very high retention of modulus. Although the partially constrained fibers shrank during heat treatment, they did not undergo any appreciable changes in length on consolidation. Thus heat treatment at temperatures above composites consolidation temperature can substantially reduce fiber shrinkage during consolidation. Taking the rule of mixture as the first degree of approximation, the property of the composite in the fiber direction is positively related to and is influenced by the property of the reinforcing fibers. Therefore heat treated fibers with better mechanical properties will result in than composites with higher properties than the ones made without heat treatment.

EXAMPLE 4

Preventing shrinkage of the reinforcing fibers during consolidation of the matrix appears to be very critical for retaining the fiber properties and consequently imparting higher final properties to the composite thus made. In this prospective example, the process to reduce longitudinal shrinkage by physically restricting the movement of the fiber during consolidation is described.

The process of making multifilament fibers from a copolymer of 5 mole percent polyglycolide and 95 mole percent polylactide is described next. The inherent viscosity of the polymer will be 1.7 dL/g. A one inch diameter vertical extruder with length to diameter ratio of 12 will be fitted with a melt pump and a 40-hole die to obtain a 40 filament extrudate. The diameters of the die hole will be 0.012 inches. The extrudate will pass through a chimney before being drawn by godet rolls and will be then wound and collected on 6 inch nominal diameter spools mounted on take up rolls. The multifilament fibers will be processed using the conditions listed in Table 4.

TABLE 4

Processing parameters for the above multifilament fibers

| Parameters | Value |
| --- | --- |
| Feed Zone | 192° C. |
| Transition Zone | 194° C. |
| Metering Zone | 213° C. |
| Pump | 214° C. |
| Adapter and clamp | 219° C. |
| Die | 244° C. |
| Chimney | 260° C. |
| Melt Pressure | <5000 psi. |
| Nominal Screw Speed | 15 rpm |
| Nominal Pump Speed | 26.8 rpm |
| Godet Speed | 1250 rpm |

The 40 filament extrudates or yarns will be collected and stored under inert nitrogen atmosphere. The filaments will be further drawn by a two stage process. In the first stage, the yarns are drawn at a speed ratio of 5.5 with the feed rolls being at 99° C. and the draw rolls being at 138° C. The yarns from the first stage are further re-drawn in the second stage to achieve an overall draw of 6.5; the last roller is at ambient temperature. The resultant yarn will have a denier of 1.56 gms/filament.

The determination of the consolidation temperature is described next. A temperature scan using a DSC can provide the melting point (Tm) of a semicrystalline matrix polymer, which is the lower limit of the consolidation temperature. Dynamic mechanical analysis done in a temperature sweep mode can provide the glass transition temperature, Tg, of the fiber. Below Tg, properties such as modulus or shrinkage change slowly but the change in properties is accelerated above Tg. A softening point can be defined as the temperature above which the rate of change in length (and sometimes modulus) occurs rapidly owing to faster relaxation. The upper limit of the consolidation temperature should be lower than the softening point of the fibers so that relaxation and consequent loss in property is limited or reduced. For a 95/5 PLA/PGA copolymer fiber impregnated with PCL matrix, the lower limit of the consolidation will be 60° C. (the melting point of PCL) and the upper limit will be about 130° C. (the temperature at which the mechanical properties of the 95/5 PLA/PGA polymer begins to dramatically decrease).

Non-heat treated fibers of 95/5 PLA/PGA made as per description above will be impregnated with poly(ε-caprolactone) (PCL) through solution prepregging process in which the solvent will be ethyl acetate and the concentration will be 5 to 15 percent. The fibers will be impregnated for 30 to 60 seconds and then dried under vacuum at room temperature for not less than 48 hours. The 95/5 PLA/PGA fiber volume fraction will be about 45 to 50 percent in the final prepregs. The prepregs will then be laid up with two fiber orientations. In this case, unidirectional and cross-ply laminates will be made from stacking 8 of the prepregs. The entire multi-layered laminate preform thus formed will be held between fixed clamps on all sides so that the fibers will be fixed or restrained in the assembly thus preventing any shrinkage occurring along the length of the fibers.

In an alternate embodiment of the present invention the fibers will be heat treated prior to using the fibers to form the prepreg. The previously described 95/5 PLA/PGA fibers will be heat treated at 120° C. for 4 hours under tension. The tension raises the melting point of the fiber and also minimizes the lose of properties by the fiber. The fibers then can be impregnated with poly(ε-caprolactone through a solution prepregging process as previously described. It is preferred that the fibers be maintained under tension during consolidation.

Consolidation of the matrix in the restrained multi-layered laminate preform will be performed under following conditions. Although the consolidation of PCL can be achieved in the temperature range from 60° C. to 120° C.; 80° C. will be chosen as it obtained good matrix impregnation in the final composite. The dwell time for consolidation will be 10 minutes. The entire multi-layered laminate preform will be held between fixed clamps and will be heated at a rate of 5° C./min up to the consolidation temperature of 80° C. Once the consolidation temperature is reached, consolidation pressure will be applied for a dwell time of 10 minutes. And then the whole assembly will be cooled at 2° C./min to room temperature before the composite will be removed.

The consolidation pressure generally depends on a variety of parameters. For example, the pressure is dependent on the mold shape, the temperature of consolidation, the viscosity of the matrix polymer, whether vacuum is employed during molding and the orientation and amount of reinforcing fiber or textile used. Generally, the pressure will be smaller for composite with fibers oriented in directions other than unidirectional. For unidirectional laminates containing 45 percent volume fraction of fibers, we have found that the consolidation pressure generally ranges from 150 to 175 psi. There appears to be a need to increase the consolidation pressure from 175 psi to 300 psi when the fiber volume fraction increases from 45 percent to 50 percent for unidirectional composites. Although unidirectional laminates containing 50 percent volume fraction of fibers require a consolidation pressure of about 300 psi, cross-plied laminates using the same volume fraction may be consolidated a pressures as low as 140 psi.

We claim:

1. A composite produced by the process comprising the steps of:
   (a) restraining and heating biocompatible organic polymeric fibers to a temperature that is above the elevated temperature of consolidation but below the melting temperature of the biocompatible organic fibers for a time sufficient to stabilize the biocompatible organic fibers, thereby providing heat treated fibers;
   (b) contacting the heat treated fibers with a polymeric matrix to provide a preform; and
   (c) consolidating the preform by heating the preform to the consolidation temperature for a time sufficient to consolidate the preform and provide a composite.

2. The composite of claim 1 wherein the fibers are restrained during consolidation.

3. The composite of claim 2 wherein the composite is a medical device.

4. The composite of claim 3 wherein the medical device is selected from the group consisting of joint replacement prosthesis, vertebral discs, pins, rods, nails, anchors, cages, screws, plates, tissue scaffolds, staples, arrows, pledgets, catheters, clamps, hooks, buttons, snaps, couplers, vascular and urological stents, valves and clips.

5. A composite produced by the process comprising the steps of:
   (a) contacting biocompatible organic polymeric fibers with a polymeric matrix to provide a preform;
   (b) restraining at least some of the biocompatible organic fibers present in the preform; and then
   (c) consolidating the preform by heating the preform to the consolidation temperature for a time sufficient to consolidate the preform and provide the composite.

6. The composite of claim 5 wherein the medical device is selected from the group consisting of joint replacement prosthesis, vertebral discs, pins, rods, nails, anchors, cages, screws, plates, tissue scaffolds, staples, arrows, pledgets, catheters, clamps, hooks, buttons, snaps, couplers, vascular and urological stents, valves and clips.

* * * * *